United States Patent [19]

Irwin et al.

[11] Patent Number: 5,895,663
[45] Date of Patent: Apr. 20, 1999

[54] PSEUDOEPHEDRINE HYDROCHLORIDE EXTENDED-RELEASE TABLETS

[75] Inventors: Jack T. Irwin, Mattawan; Shirish A. Shah, Kalamazoo, both of Mich.

[73] Assignee: L. Perrigo Company, Allegan, Mich.

[21] Appl. No.: 08/903,019

[22] Filed: Jul. 31, 1997

[51] Int. Cl.$^6$ .................... A61K 9/22; A61K 9/36
[52] U.S. Cl. .................. 424/468; 424/465; 424/474; 424/480; 514/770; 514/777; 514/781; 514/854
[58] Field of Search .................... 424/464, 465, 424/468, 469, 474, 480, 475

[56] References Cited

U.S. PATENT DOCUMENTS

| | | | |
|---|---|---|---|
| 4,259,314 | 3/1981 | Lowey | 424/19 |
| 4,369,172 | 1/1983 | Schor et al. | 424/19 |
| 4,716,041 | 12/1987 | Kjorneas et al. | 424/468 |
| 4,990,535 | 2/1991 | Cho et al. | 514/556 |
| 4,996,061 | 2/1991 | Webb et al. | 424/475 |
| 5,085,865 | 2/1992 | Nayak | 424/472 |
| 5,451,409 | 9/1995 | Rencher et al. | 424/468 |
| B1 4,389,393 | 10/1985 | Schor et al. | 424/19 |

FOREIGN PATENT DOCUMENTS

WO 94/28880  12/1994  European Pat. Off. .

*Primary Examiner*—Thurman K. Page
*Assistant Examiner*—James M. Spear
*Attorney, Agent, or Firm*—Price, Heneveld, Cooper, Dewitt & Litton

[57] ABSTRACT

Pseudoephedrine hydrochloride extended-release tablets including a sustained release hydroxypropylmethylcellulose matrix and a microcrystalline cellulose disintegrant formed by a dry mixed, direct compression method.

45 Claims, No Drawings

PSEUDOEPHEDRINE HYDROCHLORIDE EXTENDED-RELEASE TABLETS

BACKGROUND OF THE INVENTION

The advantages of sustained release products are widely recognized in the art and are of extreme importance in the pharmaceutical field. Through the use of such products, orally administered medications can be delivered continuously at a uniform rate over a prolonged period of time so as to provide a stable, predetermined concentration of a drug in the bloodstream, without requiring close monitoring and frequent re-administration.

The sustained release character of such products is achieved by one of two methods: 1) providing a sustained release coating upon tablets or microspheres wherein slow release of the active occurs via either gradual permeation through or gradual breakdown of this coating or 2) providing a sustained release matrix, such as a fat, a wax, or a polymeric material intermixed with the active ingredient in the tablet itself. See, e.g., Manford Robinson, "Sustained Action Dosage Forms" in The Theory and Practice of Industrial Pharmacy, ch. 14 (L. Lachman et al., eds., 2d ed., 1976).

Such sustained release matrix formulations are typically prepared by methods involving pre-granulating the active ingredient together with the matrix material via a wet granulation, solvent granulation, shear-melt or roto-melt granulation, or a wet pre-adsorption technique. In these techniques, a liquid phase is used in order to uniformly mix and/or closely contact the ingredients together so as to provide an evenly distributed matrix in intimate association with the active ingredient. These formation processes help prevent creation of interspersed quick-release zones which would result in discontinuous dissolution of the tablet and thus cause bioconcentration spikes of active ingredient in the patient. They frequently also result in tablets of a relatively higher density than the dry mixed ones, thus allowing the use of tablets, for a given dose, that are smaller than those made by dry mixing for the same intended release rate.

However, these liquid phase methods require a multiplicity of steps and equipment for storage, handling, and dispensing of liquids, for drying, and/or for heating of the ingredients. When the liquid is water, its volume must be very carefully controlled so as to prevent any disintegrant in the formula from swelling. Also, water is incompatible with hygroscopic active ingredients. Yet, when the liquid is instead a volatile organic solvent, additional precautions must be taken to address the risks of fire, explosion, and worker exposure. Where a melt processing technique is used, heating presents a risk of inactivation of at least some of the active material and is incompatible for use with some active ingredients.

Thus, dry mixing has sometimes been used to form sustained release matrix tablets. This technique involves pre-mixing the matrix material with the active ingredient, without the use of added liquids or heat, so that only ambient humidity, temperature, and particle-to-particle surface interactions and/or static electrical attraction foster adherence, if any, of the ingredients to one another.

For example, U.S. Pat. No. 4,259,314 to Lowey employs a mixture of cellulose ethers—hydroxypropylmethylcellulose ("HPMC") and hydroxypropyl cellulose—to form a sustained release matrix in which the cellulose ether mixture has a weighted average viscosity rating of 250–4500 cps, and preferably 1200–2900 cps. These are equilibrated under an atmosphere having up to 40% relative humidity and then pre-mixed together before drying to a moisture content of 1% or less. The active and other remaining ingredients (after they have equilibrated under $\leq 40\%$ humidity) are combined with the cellulose ether mixture and the resulting combination is compressed at $\leq 40\%$ humidity to produce a tablet.

U.S. Pat. No. 5,451,409 to Rencher et al. discloses a dry mixed pseudoephedrine tablet in which a mixture of hydroxypropyl cellulose and hydroxyethyl cellulose forms the sustained release matrix; 0.5–10% HPMC is also added as a binder.

U.S. Pat. No. 5,085,865 to Nayak discloses a two-layer tablet wherein one layer, which may be formed using a dry mixing process, comprises a 60 mg pseudoephedrine controlled release matrix formulation. The matrix or "sustained release agent" comprises cellulose ethers—hydroxypropyl and/or hydroxyethyl cellulose—and, preferably also, sodium croscarmelose; this agent is present in an amount equivalent to at least twice that of pseudoephedrine. Up to half of the cellulose ether component may consist of HPMC.

SUMMARY OF THE INVENTION

The present invention comprises extended-release tablets of an active ingredient, a sustained release HPMC matrix and a microcrystalline cellulose disintegrant. A dry mixing, direct compression method for producing such tablets is also claimed.

DETAILED DESCRIPTION OF THE PREFERRED EMBODIMENTS

In a preferred embodiment of the present invention a combination comprising at least one active ingredient together with hydroxypropylmethylcellulose (HPMC) and microcrystalline cellulose is directly compressed to form tablets. Preferably, the composition is prepared by dry mixing the ingredients.

Preferably, one of the active ingredients is pseudoephedrine or a pharmacologically acceptable salt thereof, such as pseudoephedrine hydrochloride or pseudoephedrine sulfate, or a mixture thereof. More preferred is pseudoephedrine hydrochloride. Preferably about 15–25% of the active ingredient, based on the final weight of the tablets, is used; more preferably, about 16–22%; most preferably about 17–20%. In a preferred embodiment, the amount of active ingredient used is that which is sufficient to produce tablets, each comprising about 120 mg of active ingredient. In an alternate embodiment, the amount of active utilized is sufficient to produce tablets comprising about 60 mg of active ingredient each.

The HPMC preferably has a hydroxypropyl content of less than 9% and a molecular weight below 50K. More preferably, the molecular weight is below about 30K. A preferred HPMC is Methocel® K100LV (produced by The Dow Chemical Co. of Midland, Mich.). Preferably about 20–40% HPMC is used, more preferably about 25–30%.

Suitable microcrystalline cellulose products include Emcocel® (produced by the Edward Mendell Co. of Patterson, N.Y.), Avicel® (produced by FMC Corp. of Philadelphia, Pa.), and mixtures thereof. In a preferred embodiment, about 25–50%, by final weight of the tablets, of microcrystalline cellulose is used, more preferably about 25–30%. Not more than a combined amount of about 80% (by final weight of the tablets) of disintegrant/binder and HPMC should be used. Also, the amount of microcrystalline cellulose should not substantially exceed that of HPMC, e.g., by more than 20–25% by weight.

Glidants, fillers, and other excipients that may be used in the preferred embodiments include those described, e.g., in Handbook of Pharmaceutical Excipients (J. C. Boylan et al., eds., 1986) and in H. A. Lieberman et al., Pharmaceutical Dosage Forms: Tablets (2d ed. 1990). Excipients generally may include: binders and adhesives; disintegrants, absorbents, and adsorbents; glidants and lubricants; fillers and diluents; and colorants, sweeteners, and flavoring agents.

Preferred fillers include calcium salts and sugars, for example, calcium phosphates, calcium sulfates, mannitol, lactose, and mixtures thereof. More preferred fillers include dicalcium phosphate, tribasic calcium phosphate, directly compressible calcium sulfate, directly compressible mannitol, anhydrous lactose, flowable lactose (e.g., Fast Flo® lactose produced by Foremost Farms USA of Baraboo, Wis.), and mixtures thereof. Most preferred is dicalcium phosphate (CaHPO). Preferably, about 20–40% by weight filler, based on the final weight of the tablets, is employed. However, where the filler consists of one or more sugars alone, preferably about 20–30% of filler is used.

Preferred glidants include colloidal silica and precipitated silica. A preferred colloidal silica is Cab-o-Sil® produced by the Cabot Corp. of Boston, Mass.; a preferred precipitated silica is Syloid® produced by W.R. Grace Co. of New York, N.Y. Preferably, about 0.2–2% by weight of glidant, based on the final weight of the tablets, is employed. Where colloidal silica alone is used, the tablets will preferably comprise about 0.2–0.8% by weight glidant, more preferably about 0.25–0.75%.

Preferred lubricants include sodium stearyl fumarate and metal stearates, alone or in combination with stearic acid. More preferred lubricants include magnesium stearate, zinc stearate, calcium stearate, and mixtures thereof, alone or in combination with stearic acid. Preferably about 0.2–2%, by final weight of the tablets, of lubricant is used, more preferably about 0.25–1.25%. For example, where magnesium stearate is the sole lubricant, the tablets preferably comprise about 0.3–0.5% lubricant; where a magnesium stearate-stearic acid mixture is used as the lubricant, about 0.25% magnesium stearate may be mixed with as much as about 1% stearic acid.

In the preferred embodiment mixing procedure, the active ingredient, e.g., pseudoephedrine, the glidant, e.g., colloidal silica and the filler, e.g., dicalcium phosphate dihydrate, are passed through a security screen into a clean and dry blender, preferably in the order indicated. After mixing for 5 minutes, this mix is milled through a clean and dry mill equipped with a stainless steel, drilled hole screen, into a clean suitable container.

The microcrystalline cellulose disintegrant, the above milled mixture and the hydroxypropylmethylcellulose are then passed in the order indicated through a fine mesh security screen and into a clean and dry blender. They are mixed for 15 minutes, following which a lubricant, e.g., magnesium stearate is screened into the blender and mixed in for an additional 3 minutes.

After the foregoing combination has been produced with thorough mixing, it is directly compressed to form tablets, i.e. any solid form, e.g., caplets. These are then coated with a pharmaceutically acceptable coating. Preferred coatings include cellulose ether-based coatings, such as HPMC-based coatings. A preferred coating is Opadry, produced by Colorcon, Inc. of West Point, Pa. Preferably about 0.54% by weight of coating is used (in terms of weight added to the uncoated tablet), more preferably about 1–2%. A wax, e.g., an edible wax such as carnauba wax may also be applied as a second coating thereover.

EXAMPLE 1

120 mg pseudoephedrine hydrochloride caplets were prepared as described above, using a Methocel K100LV matrix. These were administered, one each, to 12 human subject volunteers comprising Group A (the test group); 12 Sudafed® 12 Hour Caplets (Warner Wellcome Consumer Healthcare) were administered, one each, to 12 human subject volunteers comprising Group B (the comparison group). Plasma concentrations of the active ingredient were determined by capillary gas chromatography on plasma separated from blood samples drawn from each patient at 0, 1, 2, 3, 4, 4.5, 5, 5.5, 6, 6.5, 7, 8, 10, 12, 16, 24, 30, and 36 hours post-administration. This example demonstrates that the dry mixed, direct compression product of the present invention is bioequivalent to the national brand, 12 hour release pseudoephedrine tablets.

The above description is considered that of the preferred embodiment(s) only and it is understood that the embodiment(s) described above are merely for illustrative purposes. Variations of the methods and resulting compositions described herein as the preferred embodiment(s) of the invention may be apparent to those in this field once they have studied the above description. Such variations are considered to be within the scope of the invention, which is intended to be limited only to the scope of the claims as interpreted according to the principles of patent law, including the doctrine of equivalents.

The embodiments of the invention in which an exclusive property or privilege is claimed are defined as follows:

1. A method for producing extended-release tablets comprising the steps of:
    dry mixing at least one active ingredient with about 20% to about 40% by final tablet weight of hydroxypropylmethylcellulose (HPMC) and about 25% to about 50% by final tablet weight of microcrystalline cellulose; and directly compressing said mixture to form tablets.

2. The method according to claim 1 wherein at least one said active ingredient is selected from the group consisting of pseudoephedrine, pharmacologically acceptable pseudoephedrine salts, and mixtures thereof.

3. The method according to claim 2 wherein at least one said active ingredient is pseudoephedrine hydrochloride.

4. The method according to claim 1 wherein said active ingredient comprises about 17% to about 20% by weight of the tablet.

5. The method according to claim 1 wherein said active ingredient is present in an amount sufficient to produce tablets each comprising about 120 mg of said active ingredient.

6. The method according to claim 1 wherein said active ingredient is present in an amount sufficient to produce tablets, each comprising about 60 mg of said active ingredient.

7. The method of claim 1 in which said active ingredient, said HPMC and said microcrystalline cellulose are dry mixed with a glidant and a filler.

8. The method according to claim 7 which comprises a first step of dry mixing said active ingredient together with said glidant and said filler to form a pre-blend and a second step of milling said pre-blend; in a third step, said pre-blend is dry mixed with said microcrystalline cellulose and said HPMC to form a second blend, prior to said step of directly compressing said mixture to form said tablets.

9. The method according to claim 8 wherein said glidant is selected from the group consisting of colloidal silica, precipitated silica, and mixtures thereof.

10. The method according to claim 8 wherein said composition comprises about 0.2% to about 2% by weight of the tablets of said glidant.

11. The method according to claim 8 wherein said filler is selected from the group consisting of dicalcium phosphate, tribasic calcium phosphate, directly compressible calcium sulfate, directly compressible mannitol, anhydrous lactose, flowable lactose, and mixtures thereof.

12. The method according to claim 11 wherein said filler is dicalcium phosphate.

13. The method according to claim 7 wherein said composition comprises about 20% to about 40% by final tablet weight of said filler.

14. The method according to claim 7 further comprising the step of mixing a lubricant into said second blend before said step of directly compressing said mixture.

15. The method according to claim 1 further comprises a step of mixing a lubricant into said mixture before said step of directly compressing said mixture.

16. The method according to claim 15 wherein said lubricant is selected from the group consisting of sodium stearyl fumarate, magnesium stearate, zinc stearate, calcium stearate, mixtures thereof, and mixtures thereof with stearic acid.

17. The method according to claim 16 wherein said lubricant is magnesium stearate.

18. The method according to claim 15 wherein said tablets comprise about 0.2% to about 2% of said lubricant.

19. The method according to claim 1 further comprising the step of coating said tablets with a pharmaceutically acceptable coating.

20. The method according to claim 19 wherein said coating is a cellulose ether-based coating.

21. The method according to claim 19 wherein the weight of said coating applied to said tablets is equivalent to about 0.5% to about 4% by weight of said tablets.

22. A method for forming an extended-release tablet comprising:

(a) a first step of dry mixing an active ingredient comprising about 17% to about 20% by final tablet weight of one of pseudoephedrine, the pharmacologically acceptable salts thereof, or mixtures thereof together with a glidant comprising about 0.2% to about 2% by final tablet weight and a filler comprising about 20% to about 40% by final tablet weight to form a pre-blend and (b) a second step of milling said pre-blend (c) a third step of mixing said pre-blend with about 20% to about 40% by final tablet weight of HPMC and about 25% to about 50% by final tablet weight of microcrystalline cellulose to form a second blend;

(d) a fourth step of mixing about 0.2% to about 2% by final tablet weight of a lubricant into said second blend to form a final blend;

(e) a fifth step of directly compressing said final blend to form tablets; and (f) a sixth step of coating said tablets with a pharmaceutically acceptable coating.

23. An extended-release pharmaceutical tablet prepared by dry mixing at least one active ingredient, about 20% to about 40% by weight HPMC, and about 25% to about 50% by weight microcrystalline cellulose, and directly compressing the mixture to tablet form.

24. The tablet according to claim 23 comprising about 17% to about 20% by weight of said active ingredient.

25. The tablet according to claim 24 wherein said active ingredient is selected from the group consisting of pseudoephedrine, pharmacologically acceptable pseudoephedrine salts, and mixtures thereof.

26. The tablet according to claim 25 wherein the active ingredient is pseudoephedrine hydrochloride.

27. The tablet according to claim 23 further comprising a glidant.

28. The tablet according to claim 27 comprising about 0.2% to about 2% by weight of said glidant.

29. The tablet according to claim 28 wherein said glidant is selected from the group consisting of colloidal silica, precipitated silica, and mixtures thereof.

30. The tablet according to claim 27 further comprising a filler.

31. The tablet according to claim 30 comprising about 20% to about 40% by weight of said filler.

32. The tablet according to claim 31 wherein said filler is selected from the group consisting of dicalcium phosphate, tribasic calcium phosphate, directly compressible calcium sulfate, directly compressible mannitol, anhydrous lactose, flowable lactose, and mixtures thereof.

33. The tablet according to claim 32 wherein said filler is dicalcium phosphate.

34. The tablet according to claim 30 further comprising a lubricant.

35. The tablet according to claim 34 comprising about 0.2% to about 2% by weight of said lubricant.

36. The tablet according to claim 35 wherein said lubricant is selected from the group consisting of sodium stearyl fumarate, magnesium stearate, zinc stearate, calcium stearate, mixtures thereof, and mixtures thereof with stearic acid.

37. The tablet according to claim 36 wherein said lubricant is magnesium stearate.

38. The tablet produced according to claim 1.
39. The tablet produced according to claim 2.
40. The tablet produced according to claim 7.
41. The tablet produced according to claim 8.
42. The tablet produced according to claim 14.
43. The tablet produced according to claim 15.
44. The tablet produced according to claim 19.
45. The tablet produced according to claim 22.

* * * * *

UNITED STATES PATENT AND TRADEMARK OFFICE
CERTIFICATE OF CORRECTION

PATENT NO.  : 5,895,663
DATED       : APRIL 20, 1999
INVENTOR(S) : JACK T. IRWIN and SHIRISH A. SHAH It is certified that error appears in the above-identified patent and that said Letters Patent is hereby corrected as shown below:

Column 3, Line 54'
  "fme" should be --fine--.

Column 3, line 65;
  "0.54%" should be --0.5 -4%

Signed and Sealed this

Twenty-first Day of December, 1999

Attest:

Q. TODD DICKINSON

*Attesting Officer*    Acting Commissioner of Patents and Trademarks